(12) United States Patent
Voit

(10) Patent No.: US 6,275,651 B1
(45) Date of Patent: Aug. 14, 2001

(54) APPARATUS FOR EMITTING SCENTS

(76) Inventor: Hans Voit, Am Einfang 13A, D-82166 Graefelfing (DE)

( * ) Notice: Subject to any disclaimer, the term of this patent is extended or adjusted under 35 U.S.C. 154(b) by 0 days.

(21) Appl. No.: 09/515,751

(22) Filed: Feb. 29, 2000

(30) Foreign Application Priority Data

Mar. 1, 1999 (DE) .......................................... 299 03 663 U

(51) Int. Cl.[7] .................................................. A61H 33/12
(52) U.S. Cl. ........................................... 392/403; 422/125
(58) Field of Search ............................. 422/125, 4, 124; 392/395, 403, 390; 222/187; 261/24, 30, 139, 142, DIG. 65; 416/5; 4/524; 43/112

(56) References Cited

U.S. PATENT DOCUMENTS

| | | | |
|---|---|---|---|
| 4,595,564 | * | 6/1986 | Spector ................................. 422/125 |
| 4,603,030 | * | 7/1986 | McCarthy ................................. 422/4 |
| 5,071,621 | * | 12/1991 | Tokuhiro et al. ......................... 422/4 |
| 5,114,625 | * | 5/1992 | Gibson .................................. 261/30 |
| 5,161,646 | * | 11/1992 | Aurich et al. ......................... 222/187 |
| 5,222,186 | * | 6/1993 | Schimanski et al. ................. 392/395 |
| 5,624,230 | * | 4/1997 | Taylor et al. ............................. 416/5 |
| 5,771,503 | * | 6/1998 | Valimaa et al. .......................... 4/524 |
| 6,050,025 | * | 4/2000 | Wilbanks ............................... 43/112 |
| 6,090,349 | * | 7/2000 | Hirano ................................. 424/124 |
| 6,134,826 | * | 10/2000 | Mah ...................................... 43/112 |

FOREIGN PATENT DOCUMENTS

| | | |
|---|---|---|
| 93 08 368.8 U | 9/1993 | (DE) . |
| 298 13 461.6 U | 7/1998 | (DE) . |
| 993 884 | 6/1965 | (GB) . |
| 956770 * | 3/1997 | (JP) . |

* cited by examiner

*Primary Examiner*—Teresa Walberg
*Assistant Examiner*—Leonid Fastovsky
(74) *Attorney, Agent, or Firm*—Flynn, Thiel, Boutell & Tanis, P.C.

(57) ABSTRACT

A device (1) for emitting scented vapors. The device includes a storage vessel (19) in which scented solution is stored. A metering pump forces the solution into an evaporation dish (6) located above the storage vessel. The metering pump includes a tube (24) that houses a rotating spindle (25) that supplies the solution to the evaporation dish. The solution is heated by device (12) and the vapor dispersed by a fan (8).

20 Claims, 1 Drawing Sheet

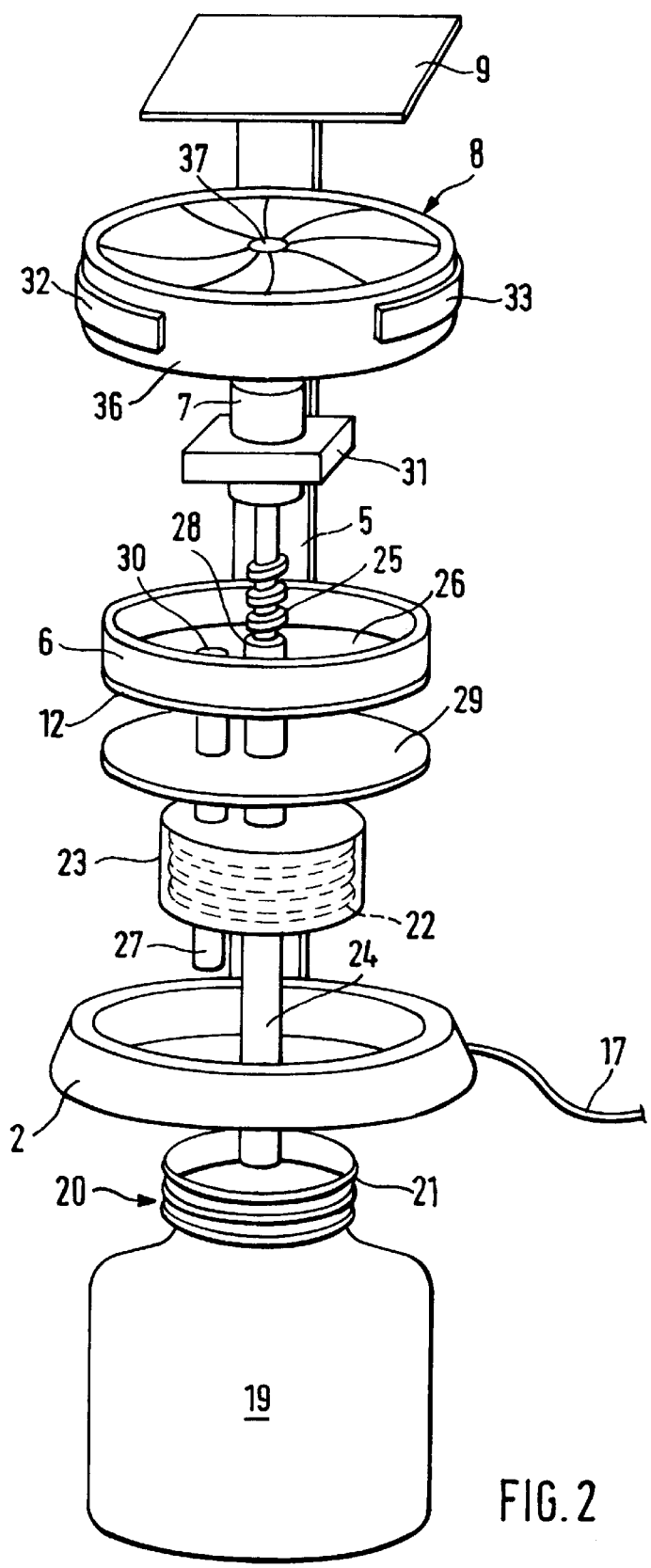
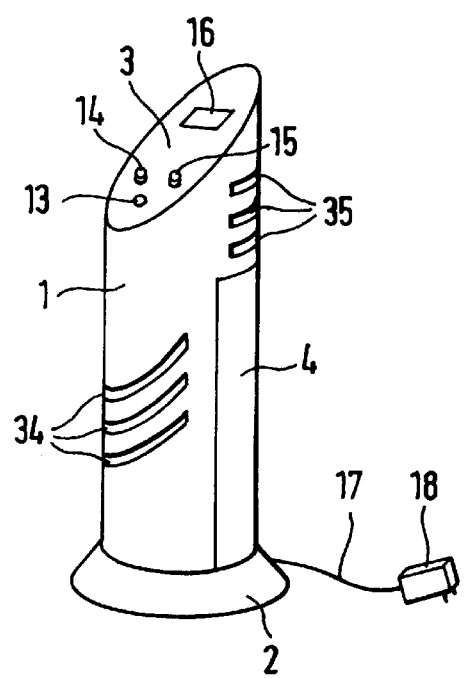
FIG. 1
FIG. 2

APPARATUS FOR EMITTING SCENTS

FIELD OF THE INVENTION

This invention relates to an apparatus for emitting scents.

BACKGROUND OF THE INVENTION

An apparatus is known (German utility model 93 08 368) for emitting scents. The known apparatus has an approximately waist-high column-shaped housing which is placed on the floor. The metering pump is formed by a hose pump connected via hoses with the storage vessel and evaporation dish. Such a hose pump is also provided in German utility model 298 13 461 having an elongate housing to be fastened to a wall or ceiling.

Known scent emitting apparatuses have proven useful by and large but they are rather voluminous. In addition, the scent solutions are sometimes quite aggressive so that the hose pump and hoses can be damaged with time.

SUMMARY OF THE INVENTION

The object of the invention is to provide a space-saving, robust, simply constructed scent emitting apparatus.

In the inventive apparatus, a metering pump is formed by a conveying or screw spindle driven by an electric motor and rotating in a tubular housing, the tube extending from the storage vessel into the bottom of the evaporation dish. The conveying spindle and the tube can thus be made of robust materials, such as metal, or a wear-resistant plastic stable to the scent solution. One can thus dispense completely without hoses coming in contact with the scent solution.

Since an electric motor with low power and thus small overall volume suffices to convey scent solution with the screw spindle, the electric motor for driving the screw spindle is preferably disposed between the evaporation dish and the fan.

The storage vessel can thus be disposed directly, or at least at a small distance, below the evaporation dish. The housing of the inventive apparatus thus has low height.

BRIEF DESCRIPTION OF THE DRAWINGS

In the following an embodiment of the inventive apparatus will be explained in more detail by way of example with reference to the drawing, in which:

FIG. 1 shows a perspective view of the scent emitting apparatus; and

FIG. 2 shows an exploded view of the apparatus without a housing.

DETAILED DESCRIPTION

According to FIG. 1, an apparatus of this invention has column-shaped housing 1 formed as a tube. Housing 1 is disposed on foot 2 and closed on the top side by oval plate 3 extending obliquely upward from the front. The housing can also have a rectangular or prismatic cross section rather than a circular one.

The back of housing 1 is adapted to be closed with cover 4 formed as a dish-shaped segment corresponding to tubular housing 1.

Housing 1, foot 2, plate 3 and cover 4 can be made of metal, e.g. injection molded light metal or sheet metal, or another material, e.g. plastic. Housing 1 with foot 2 has a height of 20 to 50 cm for example.

According to FIG. 2, foot 2 is formed as a ring having fastened thereto holding device 5 formed as a rail and extending vertically upward on the inside front of housing 1. Fastened to rail 5 from the bottom to the top are upwardly open evaporation dish 6, electric motor 7, fan 8 and board 9.

Evaporation dish 6 is heatable by electric heating device 12 which can be formed by a resistive heating element, e.g. in the form of a heating spiral, disposed on the underside of evaporation dish 6.

Board 9 holds the circuit for controlling the apparatus. Board 9 extends obliquely parallel to plate 3 closing the top of housing 1.

A switch 13, two turning knobs 14, 15 and display 16 are secured to plate 3. Switch 13 is used for switching the apparatus on and off, and for switching electric motor 7 to continuous operation during cleaning of the apparatus. Turning knob 14 is used for adjusting the fan speed, and turning knob 15 for adjusting the time intervals in which electric motor 7 is operated for scenting. For example, motor 7 can be switched on for scenting for a few seconds every hour. Display 16 can be formed by a programmable clock timer which sets the time intervals for operating motor 7.

The power supply is effected with cable 17 for connecting the apparatus to the electric network. The electric devices, i.e. electric motor 7, heating device 12 and fan 8, are operated by weak current, for example 12 volts. The necessary transformer can be disposed within plug 18. The electric lines can be fastened to holding device 5.

Scent solution is provided in storage vessel 19 disposed in housing 1 at the bottom on foot 2. Cylindrical storage vessel 19 is pushed for this purpose from the bottom to the top through ring-shaped foot 2. To be fastened in housing 1 storage vessel 19 has on neck 20 external thread 21 disposed in matching thread 22 shown by dashed lines in cup-shaped lid 23 connected with holding device 5 either directly or via evaporation dish 6.

Storage vessel 19 pushed through ring-shaped foot 2 can thus be screwed with thread 21 into internal thread 22 and thereby fastened within housing 1. Storage vessel 19 and lid 23 with matching thread 22 can be made of plastic for example.

The pump for transporting scent solution from storage vessel 19 into evaporation dish 6 is embodied by conveyor worm or screw spindle 25 driven by electric motor 7 and rotating in straight vertical tube 24.

Tube 24 extends from the lower area of storage vessel 19 to bottom 26 of evaporation dish 6 provided for this purpose with a corresponding opening. Scent solution conveyed from storage vessel 19 by screw spindle 25 emerges at the upper end of tube 24 and spreads over substantially flat bottom 26 of dish 6. Outlet opening 28 of tube 24 is disposed for this purpose in the middle of evaporation dish 6.

If the scent solution does not evaporate completely in dish 6 it flows back to storage vessel 29 via return tube 27 extending parallel to tube 24 and ending in the upper area of storage vessel 29. Opening 30 in bottom 26 of dish 6 in which return tube 27 ends is disposed off-center.

FIG. 2 shows an exploded view of lid 23 and dish 6. In reality they are close together, i.e. lid 23 can also be fastened to dish 6 or heating element 12. In order to thermally separate dish 3, in particular its electric heating element 12, from lid 23 or storage vessel 19 one provides a heat-insulating layer in the form of disk 29 of heatinsulating material between dish 6 and lid 23, both separating disk 29 and lid 23 being penetrated by tubes 24 and 27.

Electric motor 7 is inserted into a circular opening in holding plate 31 fixed on holding device 5. The holding of fan 8 is effected by flexible arms 32, 33 encompassing the circumference of fan housing 36 and fastened to holding device 5.

Circular evaporation dish 6 can be made of an aluminum material for example. Foot 2, vessel 19 with thread 21, tube 24 with screw spindle 25, lid 23, dish 6, the shaft of motor 7 and/or likewise vertically disposed shaft 37 of fan 8 are preferably disposed coaxially in housing 1.

Slot-shaped air inlet openings 34 are provided on the front of housing 1 below fan 8 in the area of evaporation dish 6 and therebelow, while slot-shaped air outlet openings 35 are provided on back 1 of the housing in the area above fan 8 and below obliquely extending board 9.

To clean the apparatus, one fills storage vessel 9 with solvent instead of scent solution. With switch 13 one can then switch electric motor 7 to continuous operation for flushing tubes 24 and 27, screw spindle 25 and evaporation dish 6.

The inventive apparatus can be placed e.g. on a cupboard, shelf, counter or table and used for scenting small rooms, e.g. offices or in the private area.

What is claimed is:

1. An apparatus for emitting scents, said apparatus comprising:
    a housing;
    a storage vessel disposed in said housing for holding scent solution;
    an upwardly directed evaporation dish disposed in said housing above said storage vessel, said evaporation dish including an electric heating device adjacent said evaporation dish for heating scent solution in said evaporation dish;
    a fan disposed in said housing above said evaporation dish for blowing evaporated solution out of said housing; and
    a metering pump disposed in said housing for pumping scent solution from said storage vessel into said evaporation dish, said metering pump including: a tube that extends from said storage vessel to said evaporation dish; a screw spindle rotatingly disposed in said tube that extends from said storage vessel to above said evaporation dish; and an electric motor attached to said screw spindle for rotating said screw spindle.

2. The apparatus according to claim 1, wherein the tube extends into a bottom portion of the evaporation dish.

3. The apparatus according to claim 1, wherein an outlet opening of the tube is disposed in a middle portion of the evaporation dish.

4. The apparatus according to claim 1, wherein the electric motor is disposed above the evaporation dish and below the fan.

5. The apparatus according to claim 1, further including a return tube that extends from the bottom of the evaporation dish to the storage vessel portion.

6. The apparatus of claim 5, wherein said return tube extends vertically.

7. The apparatus according to claim 1, wherein the tube in which the screw spindle rotates extends vertically.

8. The apparatus according to claim 1, wherein the housing has a ring-shaped foot through which the storage vessel is pushed into the housing.

9. The apparatus according to claim 8, wherein the storage vessel has a screw thread and the housing has a screw thread to which the storage vessel screw thread is mated.

10. The apparatus according to claim 9, wherein the housing screw thread is provided in a lid for closing the storage vessel.

11. The apparatus according to claim 10, further include a heat-insulating layer disposed between the storage vessel and the lid.

12. The apparatus according to claim 1, wherein the housing is formed as a column.

13. The apparatus according to claim 1, wherein the housing has at least one air inlet opening located at or below the evaporation dish, and at least one air outlet opening above the fan.

14. The apparatus according to claim 1, wherein the housing has a top member formed as a plate that extends obliquely.

15. The apparatus according to claim 13, wherein the air outlet opening is formed in a back surface of the housing.

16. The apparatus according to claim 14, wherein an operating device or display device is disposed on the plate.

17. The apparatus of claim 1, wherein at least one of the evaporation dish, the tube and the screw spindle of said pump, the motor of said pump and said fan is disposed coaxially with the storage vessel.

18. The apparatus of claim 17, further including a lid disposed in the housing, wherein the storage vessel is removably secured to the lid and the tube and screw spindle of the pump are coaxial with and extend through said lid.

19. The apparatus of claim 17, wherein the storage vessel, the tube and screw spindle of said pump, the motor of said pump and said fan are coaxially aligned.

20. The apparatus of claim 1, further including a lid disposed in the housing, wherein the storage vessel is removably secured to the lid and the tube and screw spindle of the pump extend through said lid.

\* \* \* \* \*